United States Patent [19]

Müller et al.

[11] Patent Number: 4,766,144
[45] Date of Patent: Aug. 23, 1988

[54] 3-CARBAMOYL-4-HYDROXY-COUMARINS FOR COMBATING PARASITIC HEIMINTHS

[75] Inventors: Nikolaus Müller, Monheim; Eckart Kranz; Peter Andrews, both of Wuppertal, all of Fed. Rep. of Germany

[73] Assignee: Bayer Aktiengesellschaft, Leverkusen, Fed. Rep. of Germany

[21] Appl. No.: 35,543

[22] Filed: Apr. 3, 1987

[30] Foreign Application Priority Data

Apr. 18, 1986 [DE] Fed. Rep. of Germany ....... 3613065

[51] Int. Cl.$^4$ .................... C07D 311/12; A61K 31/37
[52] U.S. Cl. .................................. 514/457; 514/337; 549/285; 546/269
[58] Field of Search ......................... 549/285; 546/269; 514/457, 337

[56] References Cited

U.S. PATENT DOCUMENTS 3,511,856 5/1970 McIntyre et al. .................... 549/285
3,991,204 11/1976 Pankavich ............................ 514/457
4,078,075 3/1978 Beriger ............................... 514/457

OTHER PUBLICATIONS

Franz et al. CA 96: 142706r.

*Primary Examiner*—Jane T. Fan
*Attorney, Agent, or Firm*—Sprung Horn Kramer & Woods

[57] ABSTRACT 3-carbamoyl-4-hydroxy-couramins for combating parasitic helminths of the formula

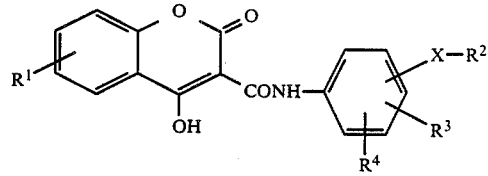

in which
$R^1$ represents hydrogen, halogen, alkyl, $NO_2$, CN or alkoxy,
X represents O, S, SO or $SO_2$
$R^2$ represents alkyl, halogenoalkyl, phenyl, naphthyl or pyridyl, which can optionally be substituted; or the radical $-X-R^2$, together with the radical $R^3$ can also form an alkylenedioxy (-O-alk-O), halogenoalkylenedioxy, oxyalkyleneoxyalkylene (-O-Alk-O-Alk-) or oxyhalogenoalkyleneoxyhalogenoalkylene bridge; and
$R^3$ and $R^4$ independently of one another represent hydrogen, halogen, CN, OH, $NO_2$, amino, mono- or dialklylamino, alkyl, halogenoalkyl, aralkyl or aryl, which can optionally be substituted, can be used for combating parasitic helminths.

8 Claims, No Drawings

3-CARBAMOYL-4-HYDROXY-COUMARINS FOR COMBATING PARASITIC HELMINTHS

The present invention relates to the use of 3-carbamoyl-4-hydroxy-coumarins for combating parasitic helminths, new 3-carbamoyl-4-hydroxy-coumarins and their preparation.

3-Carbamoyl-4-hydroxycoumarins with an anthelmintic action have already been disclosed. However, their action is not always satisfactory, especially when low concentrations are applied.

1. It has been found that the 3-carbamoyl-4-hydroxycoumarins of the general formula

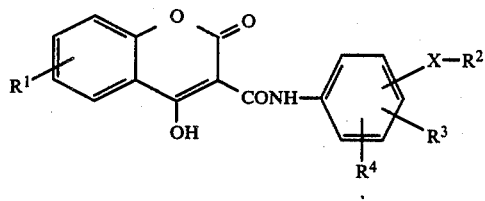

in which
   $R^1$ represents hydrogen, halogen, alkyl, $NO_2$, CN or alkoxy,
   X represents O, S, SO or $SO_2$
   $R^2$ represents alkyl, halogenoalkyl, phenyl, naphthyl or pyridyl, which can optionally be substituted; or the radical —X—$R^2$, together with the radical $R^3$ can also form an alkylenedioxy (—O—Alk—O), halogenoalkylenedioxy, oxyalkyleneoxyalkylene (—O—Alk—O—Alk—) or oxyhalogenoalkyleneoxyhalogenoalkylene bridge; and
   $R^3$ and $R^4$ independently of one another represent hydrogen, halogen, CN, OH, $NO_2$, amino, mono- or dialkylamino, alkyl, halogenoalkyl, aralkyl or aryl, which can optionally be substituted,
can be used for combating parasitic helminths. The compounds of the formula I can exist in their various tautomeric forms and as mixtures of these tautomeric forms:

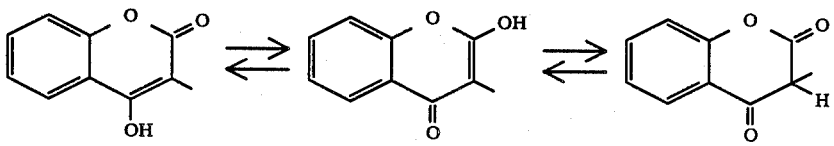

2. The new 3-carbamoyl-4-hydroxycoumarins of the general formula

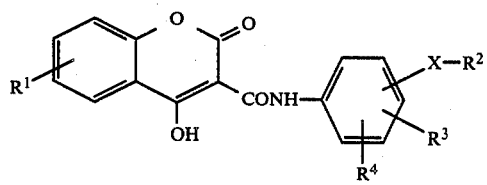

in which
   $R^1$ represents hydrogen, halogen, alkyl, $NO_2$, CN or alkoxy,
   X represents O, S, SO or $SO_2$,
   $R^2$ represents phenyl, naphthyl or pyridyl, which can optionally be substituted, and
   $R^3$ and $R^4$ independently of one another represent hydrogen, halogen, CN, OH, $NO_2$, amino, mono- or dialkylamino, alkyl, halogenoalkyl, aralkyl, aryl, which can optionally be substituted,
but excluding 4-hydroxy-3-[4-(4-chlorophenoxy)-phenylcarbamoyl]-coumarin have been found.

3. It has been found that the 3-carbamoyl-4-hydroxycoumarins of the formula I

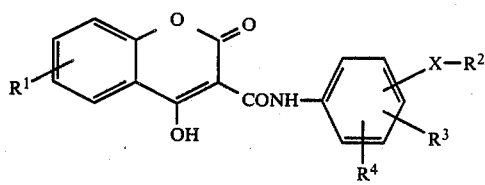

in which
   $R^1$ represents hydrogen, halogen, alkyl, $NO_2$, CN or alkoxy,
   X represents O, S, SO or $SO_2$
   $R^2$ represents phenyl, naphthyl or pyridyl, which can optionally be substituted, and
   $R^3$ and $R^4$ independently of one another represent hydrogen, halogen, CN, OH, $NO_2$, amino, mono- or dialkylamino, alkyl, halogenoalkyl, aralkyl, aryl, which can optionally be substituted,
but excluding 4-hydroxy-3-[4-(4-chlorophenoxy)-phenylcarbamoyl]-coumarin, are obtained by a process in which (a) 4-hydroxycoumarins of the formula II

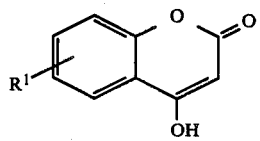

in which
   $R^1$ has the abovementioned meaning, are reacted with isocyanates of the formula III

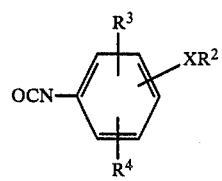

in which
   X, $R^2$, $R^3$ and $R^4$ have the abovementioned meaning, or (b) 4-hydroxycoumarin-3-carboxylic acid esters of the formula IV

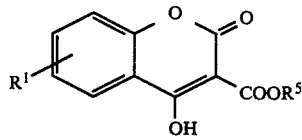

in which
R¹ has the abovementioned meaning and
R⁵ represents $C_{1-4}$-alkyl, phenyl or 4-$NO_2$-phenyl are reacted with amines of the formula VI
in which

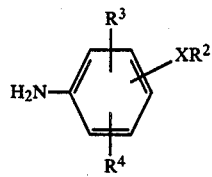

X, $R^2$, $R^3$ and $R^4$ have the abovementioned meaning.

Compounds of the formula I which are preferably employed are those
in which
R¹ represents hydrogen, fluorine, chlorine, bromine, $C_{1-4}$-alkyl, $NO_2$, CN or $C_{1-4}$-alkoxy,
X represents O or S,
R² represents $C_{1-4}$-alkyl, $C_{1-4}$-halogenoalkyl, phenyl, naphthyl or pyridyl, which are optionally substituted by one or more of the following radicals: alkyl with preferably 1 to 4, in particular 1 or 2, carbon atoms, such as methyl, ethyl, n.- or i.-propyl or n.-, i.-, s.- or t.-butyl; alkoxy with preferably 1 to 4, in particular 1 or 2, carbon atoms, such as methoxy, ethoxy, n.- or i.-propoxy or n.-, i.-, s.- or t.-butoxy; alkylthio with preferably 1 to 4, in particular 1 or 2, carbon atoms, such as methylthio, ethylthio, n.- or i.-propylthio or n.-, i.-, s.- or t.-butylthio; halogenoalkyl with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl or fluorochloroethyl; halogenoalkoxy with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethoxy; halogenalkylthio with preferably 1 to 4, in particular 1 or 2, carbon atoms and preferably 1 to 5, in particular 1 to 3, halogen atoms, the halogen atoms being identical or different and halogen atoms being, preferably, fluorine, chlorine or bromine, in particular fluorine, such as trifluoromethylthio; alkylenedioxy with preferably 1 or 2 carbon atoms, such as methylenedioxy or ethylenedioxy; halogen-substituted alkylenedioxy with preferably 1 or 2 carbon atoms and preferably 1 to 4, in particular 2 or 3, halogen atoms, the halogen atoms being identical or different and halogen atoms being, preferably, fluorine or chlorine, in particular fluorine, such as difluoromethylenedioxy, trifluoroethylenedioxy or tetrafluoroethylenedioxy; oxyalkylene-oxyalkylene, in particular oxymethyleneoxymethylene (—O—CH₂—O—$CH_2$—), which can optionally be one or polysubstituted by halogen, in particular fluorine or chlorine, preferably oxydifluoromethyleneoxydifluoromethylene; hydroxyl; halogen, preferably fluorine, chlorine, bromine or iodine, in particular chlorine or bromine; cyano; nitro; amino; monoalkyl- and dialkylamino with preferably 1 to 4, in particular 1 or 2, carbon atoms per alkyl group, such as methylamino, methyl- ethyl- amino, n.- or i.-propylamino or methyl-n.-butylamino; formyl; carboxyl; alkylcarbonyl with preferably 2 to 4 carbon atoms, in particular acetyl; carbalkoxy with preferably 2 to 4, in particular 2 or 3, carbon atoms, such as carbomethoxy and carbethoxy; sulpho (—$SO_3H$); alkylsulphonyl with preferably 1 to 4, in particular 1 or 2, carbon atoms, such as methylsulphonyl or ethylsulphonyl; halogenalkylsulphonyl with preferably 1-2 carbon atoms and 1-3 halogen atoms, the halogen atoms being identical or different and halogen atoms being, preferably, fluorine or chlorine, such as trichloromethylsulphonyl or trifluoromethylsulphonyl; arylsulphonyl with preferably 6 or 10 aryl carbon atoms, such as phenylsulphonyl; and phenyl, naphthyl, phenoxy, naphthoxy, phenylthio and naphthyl-thio, which can in turn be further substituted.

The radical —X—R², together with radical R³ in the ortho-position relative to this radical, preferably represents an alkylenedioxy, in particular methylenedioxy or ethylenedioxy, bridge or an oxyalkyleneoxyalkylene, in particular oxymethyleneoxymethylene, bridge, which is optionally substituted by one or more identical or different halogen atoms, in particular fluorine or chlorine.

The following bridges may be mentioned as particularly preferred: methylenedioxy, ethylenedioxy, difluoromethylenedioxy, dichloromethylenedioxy, tetrafluoroethylenedioxy, trifluorochloroethylenedioxy, oxymethyleneoxymethylene and oxydifluoromethyleneoxydifluoromethylene.

R³ and R⁴ independently of one another preferably represent hydrogen, halogen, in particular fluorine, chlorine or bromine, CN, OH, $NO_2$, amino, monoalkyl- or dialkylamino with preferably 1 to 4, in particular 1 or 2, carbon atoms per alkyl group, such as methylamino, methyl-ethyl-amino, n.- or i.-propylamino or methyl-n.-butylamino; alkyl with preferably 1 to 4, in particular 1 or 2, carbon atoms, such as methyl, ethyl, n.- or i.-propyl or n.- i.-, s.- or t.-butyl; halogenoalkyl with preferably 1 to 4, in particular 1 or 2 carbon atoms and preferably 1 to 5, in particular 1 to 3, halogen atoms, the halogen atoms being identical or different and halogen atoms being, preferably, fluorine, chlorine or bromine, in particular fluorine, such as trifluoromethyl or fluorochloroethyl; aralkyl with 1-4 carbon atoms, in particular 1 or 2 carbon atoms, in the alkyl part and preferably phenyl in the aryl part, which can preferably be substituted by one of the substituents mentioned above, or phenyl, naphthyl or pyridyl, which can preferably be substituted by one of the substituents mentioned above.

Compounds of the formula I which are particularly preferably employed are those
in which
R¹ represents hydrogen, methyl,
X represents O or S,
R² represents $C_{1-4}$-alkyl, in particular methyl, or $C_{1-4}$-halogenoalkyl, in particular trifluoromethyl, or represents phenyl or pyridyl, which are optionally substituted by one or more of the following radicals: $C_1$-$C_4$-alkyl, in particular methyl, $C_1$-$C_4$-alkoxy, in particular methoxy or ethoxy, $C_1$-$C_4$-halogenoalkoxy, in particular trifluoromethoxy or fluoro-chloroethoxy, $C_1$-$C_4$-halogenoalkylthio, in particular trifluoromethylthio, $C_1$-$C_4$-alkylthio, in particular methylthio, $C_1$-$C_4$-alkylsulphonyl, in particular methylsulphonyl, $C_1$-$C_4$-halogenoalkylsulphonyl, in particular trifluoromethylsulphonyl, $C_1$-$C_4$-halogenoalkyl, in particular trifluoromethyl, methylenedioxy or ethylenedioxy, which are optionally substituted by fluorine or chlorine, halogen, in particular fluorine or chlorine, or $NO_2$, and $R^3$ and $R^4$ independently of one another represent hydrogen, halogen, in particular chlorine or fluorine, $C_{1-4}$-alkyl, in particular methyl, or $C_{1-4}$-halogenoalkyl, in particular trifluoromethyl.

Compounds of the formula I which are especially preferably employed are those
in which
$R^1$ represents hydrogen, methyl,
X represents O,
$R^2$ represents phenyl, which is optionally substituted by one or more of the abovementioned radicals, in particular by $C_{1-4}$-halogenoalkyl, especially trifluoromethyl, and
$R^3$ and $R^4$ represent hydrogen.

The new 3-carbamoyl-4-hydroxycoumarins according to 2 (above) are obtained by a procedure in which, for example, 4-hydroxycoumarin is reacted with trifluoromethylphenoxyphenylisocyanate in accordance with process (3a).

The course of the reaction can be represented by the following equation:

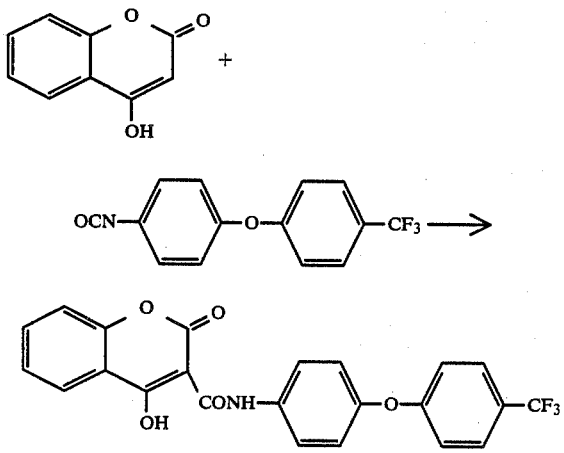

Formula (III) provides a general definition of the isocyanates required as starting substances for the process according to the invention. In the formula, X, $R^2$, $R^3$ and $R^4$ preferably represent the radicals which have already been mentioned as preferred for these substituents in the case of the substances of the formula (I).

The following isocyanates of the formula (III) may be mentioned specifically: 4-trifluoromethoxyphenyl isocyanate, 4-trifluoromethylthio-phenyl isocyanate, 3-chloro-4-trifluoromethylphenyl isocyanate, 4-trifluoromethylsulphonylphenyl isocyanate, 4-tetrafluoroethoxyphenyl isocyanate, 4-methoxy-, 4-trifluoromethoxy-and 4-trifluoromethylthiophenoxyphenyl isocyanate and 4-trifluoromethylphenoxy-phenyl isocyanate.

The isocyanates of the formula (III) are known or they can be prepared in a generally known manner.

The 4-hydroxycoumarins of the formula II also to be used as starting substances are likewise generally known compounds of organic chemistry.

Compounds of the formulae II and III are reacted in the presence of diluents and in the presence of bases, and, if appropriate, in the presence of other catalysts.

Bases which may be mentioned are: alkali metal and alkaline earth alcoholates and tertiary amines. The following bases may be mentioned as particularly preferred: triethylamine, pyridine, picolines, trimethylamine, N-methylmorpholine, N-ethylpyrrolidine, diazabicyclo(4,3,0)undecene (DBU), 1,4-diaza-bicyclo-2,2,2-octane (DABCO), diazabicyclo(3,2,0)nonene (DBN).

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, tetrachlorocarbon, chlorobenzene and o-dichlorobenzene, and furthermore ethers, such as diethyl ether, dibutyl ether, glycol dimethyl ether, diglycol dimethyl ether, tetrahydrofuran and dioxane, and moreover ketones, such as acetone, methyl ethyl ketone, methyl isopropyl ketone and methyl isobutyl ketone, and also esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethylsulphoxide, tetramethylenesulphone and hexamethylphosphoric acid triamide.

Possible catalysts are the customary catalysts in reactions with isocyanates. Catalysts which may be mentioned are: metal catalysts of Zn, Sn and Pb, such as dibutyl-tin dilaurate, dibutyl-tin dioxide, tin octoate, lead octoate, zinc octoate, zinc chloride and zinc acetate.

The reaction is carried out between 0° and 150° C., preferably between 20° and 50° C. The reaction is preferably carried out under normal pressure.

The compounds of the formulae II and III are employed in equimolar amounts, and a slight excess of one or the other of the components provides no substantial advantages.

Working up is carried out in a manner which is known per se, for example by adding dilute acid to the reaction mixture and filtering off the products or separating off the organic phase and distilling off the solvent.

If methyl 4-hydroxycoumarin-3-carboxylate is employed as the compound of the formula IV and 3-phenoxy-4-chloroaniline is employed as the amine of the formula V in process 3d, the process can be represented by the following equation:

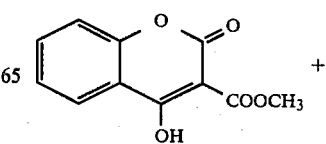

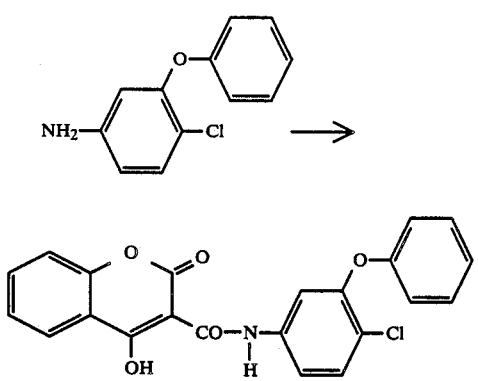

The compounds of the formula IV are known or can be prepared by a process analogous to known processes. Preferred compounds of the formula IV are those in which $R^1$ has the meanings mentioned as preferred and particularly preferred in the case of the compounds of the formula I, and in which $R^5$ represents methyl, ethyl or p-nitrophenyl.

The amines of the formula V are known or can be prepared by processes analogous to known processes.

Amines of the formula V in which the substituents X, $R^2$, $R^3$ and $R^4$ have the meanings mentioned as preferred and particularly preferred in the case of the compounds of the formula I are preferably employed.

The following compounds of the formula V may be mentioned specifically: 4-trifluoromethoxy aniline, 4-trifluoromethylmercaptoaniline, 3-chloro-4-trifluoromethoxy aniline, 3-chloro-4-trifluoromethylmercaptoaniline, 3-nitro-4-trifluoromethoxyaniline, 4-(1,1,2,2-tetrafluoroethoxy)-aniline, 2,6-dichloro-4-trifluoromethylmercaptoaniline, 4-amino-4'-trifluoromethyl-diphenyl ether and 4-amino-3'-trifluoromethyl-diphenyl ether.

The reaction of the compounds of the formula IV and V is preferably carried out in the presence of diluents and in the presence of bases.

Possible diluents are all the inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, and furthermore ethers, such as diethyl ether, dibutyl ether, glycol dimethyl ether, diglycol dimethyl ether, tetrahydrofuran and dioxane, and moreover ketones, such as acetone, methyl ethyl ketone, methyl isopropyl ketone and methyl isobutyl ketone, and also esters, such as methyl and ethyl acetate, and furthermore nitriles, such as, for example, acetonitrile, propionitrile, benzonitrile and glutaric acid dinitrile, and moreover amides, such as, for example, dimethylformamide, dimethylacetamide and N-methylpyrrolidone, as well as dimethylsulphoxide, tetramethylenesulphone and hexamethylphosphoric acid triamide, and furthermore alcohols, such as methanol, ethanol, propanol or butanol.

Bases which may be mentioned are alkali metal and alkaline earth metal hydroxides and alkali metal and alkaline earth metal alcoholates, in particular sodium methylate or ethylate.

The reaction is carried out between 50° and 150° C., preferably between 60° and 110° C. It is preferably carried out under normal pressure.

The compounds of the formulae VI and VII are employed in equimolar amounts, and a slight excess of one or the other of the components provides no substantial advantages.

Working up is carried out in a manner which is known per se, for example by adding water to the reaction mixture, separating off the organic phase and distilling off the solvent.

As already mentioned, the active compounds of the formula I have a broad action against parasitic helminths. Above all, they have an action against trematodes and nematodes, in particular liver fluke and gastric and intestinal nematodes in ruminants. They moreover all have an action against those gastric and intestinal nematodes which are resistant to the usual benzimidazole anthelmintics and thus can no longer be adequately treated.

The action was tested in an animal experiment following oral, parenteral and dermal administration to experimental animals heavily infested with parasites. The dosages used were tolerated very well by the experimental animals.

The active compounds according to the invention can be used as anthelmintics.

The active compounds according to the invention can be administered together with other customary anthelmintics.

The active compounds according to the invention can be used either as such or in combination with pharmaceutically acceptable excipients. Possible presentation forms in combination with various inert excipients are tablets, capsules, granules, aqueous suspensions, injectable solutions, emulsions and suspensions, elixirs, syrups, pastes and the like. Such excipients include solid diluents or fillers, a sterile aqueous medium and various non-toxic organic solvents and the like. The tablets and the like possible for oral administration can of course also be provided with a sweetener additive and the like. In the abovementioned case, the therapeutically active compound should be present in a concentration of about 0.5 to 90% by weight of the total mixture, that is to say in amounts which are sufficient to achieve the abovementioned dosage range.

The formulations are prepared in a known manner, for example by extending the active compounds with solvents and/or excipients, if appropriate using emulsifying agents and/or dispersing agents, and, for example, in the case where water is used as the diluent, organic solvents can be used as an auxiliary solvent, if appropriate.

Examples of auxiliaries which may be mentioned are: water, non-toxic organic solvents, such as paraffins (for example petroleum fractions), vegetable oils (for example groundnut-sesame oil), alcohols (for example ethyl alcohol and glycerol), glycols (for example propylene glycol and polyethylene glycol) and water; solid excipients, such as, for example, natural rock powders (for example kaolins, aluminas, talc and chalk) synthetic rock powders (for example highly disperse silicic acid and silicates) and sugars (for example sucrose, lactose and glucose); emulsifying agents, such as non-ionic and anionic emulsifiers (for example polyoxyethylene fatty acid esters, polyoxyethylene fatty alcohol ethers, alkylsulphonates and arylsulphonates), dispersing agents (for example methylcellulose, starch and polyvinylpyrrolidone) and lubricants (for example magnesium stearate, talc, stearic acid and sodium lauryl-sulphate).

In the case of oral use, tablets can of course also contain, in addition to the excipients mentioned, additives such as sodium citrate, calcium carbonate and dicalcium phosphate, together with various adjuvants, such as starch, preferably potato starch, gelatin and the like. Lubricants, such as magnesium stearate, sodium lauryl-sulphate and talc, can furthermore be co-used for tablet-making.

In the case of aqueous suspensions and/or elixirs intended for oral use, various flavor improvers or dyestuffs can be added to the active compounds, in addition to the abovementioned auxiliaries.

In the case of parenteral use, solutions dragees, ampoules and the like can also be in the form of dosage units, each dosage unit being adapted so that it delivers an individual dose of the active constituents.

The active compounds according to the invention can also be present in the formulations in mixtures with other known active compounds used in veterinary and/or human medicine for the treatment of infections and/or diseases, and active compounds which may be mentioned in particular are L-2,3,5,6-tetrahydro-6-phenyl-imidazothiazole, benzimidazole-carbamates, praziquantel and febantel.

The active compounds can be used in the customary manner. Administration is preferably effected orally, and parenteral, in particular subcutaneous, or dermal administration (pour-on or spot-on) is possible.

In general, it has proved advantageous to administer amounts of about 1 to about 100 mg of the active compounds per kg of body weight per day to achieve effective results.

Nevertheless, it may at times be necessary to deviate from the amounts mentioned, and in particular to do so as a function of the body weight of the experimental animal or of the nature of the mode of administration, but also because of the animal species and its individual behavior towards the medicament or the nature of its formulation and the time or interval at which administration takes place. Thus in some cases it may be sufficient to manage with less than the abovementioned minimum amount, whilst in other cases the upper limit mentioned must be exceeded. Where relatively large amounts are administered, it may be advisable to divide these into several individual doses over the course of the day. The same dosage range is envisaged for administration in veterinary medicine. The other above statements also apply in the general sense.

EXAMPLE A

In vitro nematode test
*Caenorhabditis elegans*

10-4 of active compound are dissolved in 1 ml of water or 0.1 ml of dimethylsulphoxide (DMSO). This solution was introduced onto a Replica plate. 2 ml of an *E.coli* suspension into which 10–20 female animals or larvae of *Caenorhabditis elegans* in 0.5 ml or sterile M9 buffer solution had been introduced were added. The *E.coli* suspension was prepared by adding 1.8 l of sterile M9 buffer solution to 300 ml of an overnight culture of a uracil-dependent *E.coli* strain.

The test batch was incubated at 22° C. for 7 days and then evaluated. The extent to which the active compound impaired the multiplication was evaluated and the concentration at which the multiplication is prevented was stated. The following results were obtained:

TABLE a

| In vitro nematode test *Caenorhabditis elegans* | |
|---|---|
| Active compound Example No. | Effective dose (μg/ml) |
| 1 | 100 |
| 2 | 100 |
| 3 | 100 |
| 5 | 100 |
| 6 | 100 |
| 7 | 100 |
| 8 | 100 |
| 11 | 100 |

EXAMPLE B

In vivo nematode test
*Haemonchus contortus*/sheep

Sheep infected experimentally with *Haemonchus contortus* were treated after the prepatency period of the parasite had elapsed. The active compounds were administered orally as pure active compound in gelatine capsules.

The degree of action is determined by quantitative counting of the worm eggs excreted with the faeces before and after treatment.

A complete halt in the excretion of eggs after treatment means that the worms have been expelled or are damaged so that they can no longer produce eggs (effective dose).

The active compounds tested and the effective dosages can be seen from the following table:

TABLE b

| In vivo nematode test *Haemonchus contortus*/sheep | |
|---|---|
| Active compound Example No. | Effective dose in mg/kg |
| 15 | 2.5 |
| 16 | 2.5 |

PREPARATION EXAMPLES (a) General instructions on the preparation of the compounds of the formula I in accordance with process 3a.

In each case 0.03 mol of the compound II and the isocyanate (III) are taken in 120 ml of dry THF and a solution of 0.033 mol of "DBU" in 30 ml of tetrahydrofuran is added at room temperature in the course of 10 minutes. Gentle evolution of heat thereby occurs. The mixture is then subsequently stirred under reflux until conversion is complete (about 4–5 hours) and is cooled and the entire batch is stirred into 400 ml of 10% strength hydrochloric acid. The solid which thereby separates is filtered off with suction, washed with water and dried.

(b) General instructions for the preparation of the compounds of the formula I in accordance with process 3d.

0.03 mol of the ethyl ester of the formula IV and 0.03 mol of the amine of the formula V are suspended in 100 ml of toluene and the suspension is heated at the reflux temperature for about 10 hours under nitrogen, ethanol escaping. The reaction mixture is cooled and the solid is filtered off. The product filtered off is rinsed with ethanol and then dried.

EXAMPLE 1

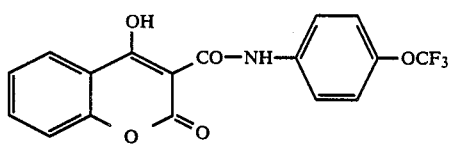

First 5.1 g (0.05 mol) of triethylamine and then, slowly, 10.2 g (0.05 mol) of 4-trifluoromethoxyphenyl isocyanate are added dropwise to 8.1 g (0.05 mol) of 4-hydroxycoumarin in 100 ml of dimethylsulphoxide at room temperature. The temperature thereby rises to 31° C. The reaction mixture is subsequently stirred at room temperature for 5 hours. It is added to a mixture of 250 ml of cold water and 15 ml of concentrated hydrochloric acid, whereupon a white precipitate separates out. The mixture is stirred for 30 minutes, with cooling, and the precipitate is filtered off with suction, rinsed with acid water and dried at 50° C. in vacuo. Recrystallization from 100 ml of dioxane gives 8.3 g (45.6% of theory) of 4-hydroxy-3-(4-trifluoromethyloxyphenyl-carbamoyl)-coumarin of melting point 194°–195° C.

The following compounds of the general formula

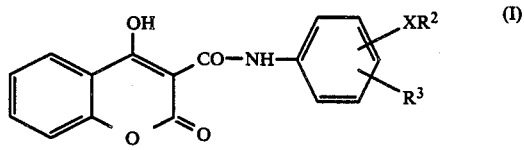

can be obtained in an analogous manner:

| Example No. | XR² | R³ | Melting point (°C.) |
|---|---|---|---|
| 2 | 4-SCF₃ | 3-Cl | 201–03 |
| 3 | 4-SCF₂Cl | 3-Cl | 206–07 |
| 4 | 4-OCF₂—CHFCl | — | 210–11 |
| 5 | 4-SCF₃ | — | 234–38 |
| 6 | 3,4-CF₂—O—CF₂—O | | 236–42 |
| 7 | 4-OCF₂—CHF—CF₃ | — | 174–78 |
| 8 | 4-OCF₂Cl | — | 189–92 |
| 9 | 4-OCH₃ | 3-CF₃ | 285–94 |
| 10 | 4-OCF₃ | 2-Cl | 182–92 |
| 11 | 3-OCF₃ | — | 160–65 |
| 12 | 4-OCF₃ | 3-Cl | 200–04 |
| 13 | 4-O—⟨⟩—Cl | 3-CF₃ | 181–88 |
| 14 | 3,4-O—CF₂—CF₂—O | | 258–63 |
| 15 | 4-O—⟨⟩—CF₃ | — | 209–211 |
| 16 | 4-O—⟨⟩—CF₃ (3-CF₃) | — | 165 |

It will be understood that the specification and examples are illustrative but not limitative of the present invention and that other embodiments within the spirit and scope of the invention will suggest themselves to those skilled in the art.

We claim:

1. A method of combating parasitic helminths which comprises applying to a host to be freed thereof an anthelminthically effective amount of a 3-carbamoyl-4-hydroxycoumarin of the formula

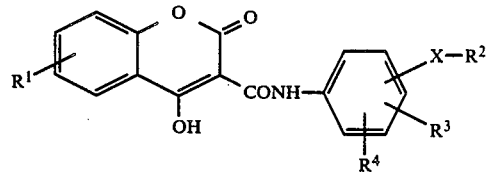

in which $R^1$ represents hydrogen, fluorine, chlorine, bromine, $C_{1-4}$-alkyl, $NO_2$, CN or $C_{1-4}$-alkoxy, X represents O or S, $R^2$ represents $C_{1-4}$-alkyl, $C_{1-4}$-halogenoalkyl, phenyl, naphthyl or pyridyl, which are optionally substituted by one or more of alkyl with 1 to 4 carbon atoms; alkoxy with 1 to 4 carbon atoms; alkylthio with 1 to 4 carbon atoms; halogenoalkyl with 1 to 4 carbon atoms and 1 to 5 halogen atoms; halogenoalkoxy with 1 to 4 carbon atoms and 1 to 5 halogen atoms; halogenoalkylthio with 1 to 4 carbon atoms and 1 to 5 halogen atoms; hydroxyl; halogen; cyano; nitro; amino; monoalkyl- and dialkylamino with 1 to 4 carbon atoms per alkyl group; formyl, carboxyl; alkylcarbonyl with 2 to 4 carbon atoms; carbalkoxy with 2 to 4 carbon atoms; sulpho (—$SO_3H$); alkylsulphonyl with 1 to 4 carbon atoms; halogenalkylsulphonyl with 1–2 carbon atoms and 1–3 halogen atoms; arylsulphonyl with 6 or 10 aryl carbon atoms; and phenyl, naphthyl, phenoxy, naphthoxy, phenylthio and naphthylthio, and $R^3$ and $R^4$ independently of one another represent hydrogen; halogen; CN; OH; $NO_2$; amino, monoalkyl- or dialkylamino with 1 to 4 carbon atoms per alkyl group; alkyl with 1 to 4 carbon atoms; halogenoalkyl with 1 to 4 carbon atoms and 1 to 5 halogen atoms; aralkyl with 1–4 carbon atoms in the alkyl part and phenyl in the aryl part, or phenyl, naphthyl or pyridyl, or —X—$R^2$ together with $R^3$ in the ortho-position relative thereto represent an alkylenedioxy bridge or an oxyalkyleneoxyalkylene bridge with 1 or 2 carbon atoms in each alkylene moiety and which is optionally substituted by one or more halogen atoms.

2. The method according to claim 1, in which $R^1$ represents hydrogen or methyl, X represents O or S, $R^2$ represents $C_{1-4}$-alkyl; $C_{1-4}$-halogenoalkyl; or phenyl or pyridyl, which is optionally substituted by one or more of $C_1$–$C_4$-alkyl, $C_1$–$C_4$-alkoxy, $C_1$–$C_4$-halogenoalkoxy, $C_1$–$C_4$-halogenoalkylthio, $C_1$–$C_4$-alkylthio, $C_1$–$C_4$-alkylsulphonyl, $C_1$–$C_4$-halogenoalkylsulphonyl or $C_1$–$C_4$-halogenoalkyl, and R³ and R⁴ independently of one another represent hydrogen, halogen, $C_1$-$C_4$-alkyl, or $C_1$-$C_4$-halogenoalkyl, or —X—R² together with R³ in the ortho-position relative thereto represent methylenedioxy or ethylenedioxy which are optionally substituted by fluorine or chlorine.

3. The method according to claim 1, in which

R¹ represents hydrogen or methyl,

X represents O,

R² represents phenyl, which is optionally substituted by $C_{1-4}$-halogenoalkyl, and R³ and R⁴ represent hydrogen.

4. The method according to claim 1, wherein such compound is 4-hydroxy-3-(4-trifluoromethyloxy-phenylcarbamoyl)-coumarin of the formula

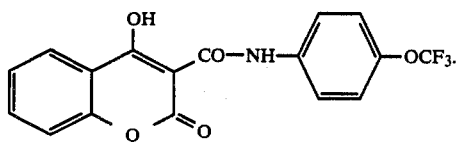

5. The method according to claim 1, wherein such compound is 4-hydroxy-3-(3-chloro-4-trifluoromethyl-thiophenyl-carbamoyl)-coumarin of the formula

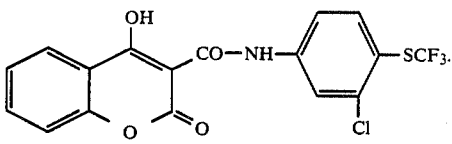

6. The method according to claim 1, wherein such compound is 4-hydroxy-3-(3-chloro-4-trifluoromethoxyphenyl-carbamoyl)-coumarin of the formula

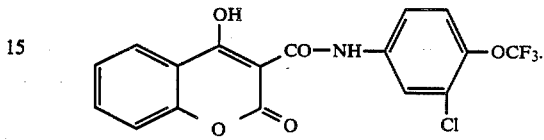

7. The method according to claim 1, wherein such compound is 4-hydroxy-3-[4-(4-trifluoromethylphenoxy)phenyl-carbamoyl]-coumarin of the formula

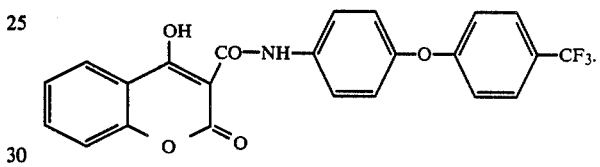

8. The method according to claim 1, wherein such compound is 4-hydroxy-3-[4-(3-trifluoromethylphenoxy)phenyl-carbamoyl]-coumarin of the formula

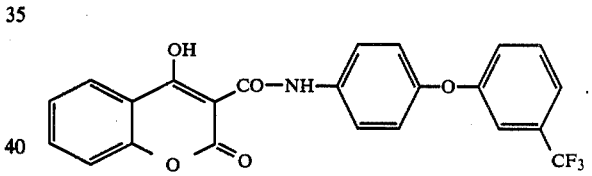

* * * * *